(12) United States Patent
Oginski et al.

(10) Patent No.: US 10,780,006 B2
(45) Date of Patent: Sep. 22, 2020

(54) MOUNTING DEVICE FOR A STAND DEVICE AND MOUNTING SYSTEM INCLUDING THE MOUNTING DEVICE

(71) Applicant: Ondal Medical Systems GmbH, Hünfeld (DE)

(72) Inventors: Stefan Oginski, Fulda (DE); Markus Höser, Tann (DE)

(73) Assignee: Ondal Medical Systems GmbH, Hünfeld (DE)

( * ) Notice: Subject to any disclaimer, the term of this patent is extended or adjusted under 35 U.S.C. 154(b) by 178 days.

(21) Appl. No.: 15/517,898

(22) PCT Filed: Oct. 19, 2015

(86) PCT No.: PCT/EP2015/002061
§ 371 (c)(1),
(2) Date: Apr. 7, 2017

(87) PCT Pub. No.: WO2016/058706
PCT Pub. Date: Apr. 21, 2016

(65) Prior Publication Data
US 2018/0228680 A1    Aug. 16, 2018

(30) Foreign Application Priority Data
Oct. 17, 2014   (EP) ..................................... 14003555

(51) Int. Cl.
*A61G 12/00* (2006.01)
*A61B 90/50* (2016.01)
(Continued)

(52) U.S. Cl.
CPC ............ *A61G 12/004* (2013.01); *A61B 90/50* (2016.02); *F16M 11/2014* (2013.01); *F16M 13/027* (2013.01)

(58) Field of Classification Search
CPC ...... A61G 12/004; A61B 90/50; A61B 90/25; F16M 11/2014; F16M 13/027;
(Continued)

(56) References Cited

U.S. PATENT DOCUMENTS 1,517,626 A * 12/1924 Weinfeld ................ F21V 21/02
248/343
2,147,284 A * 2/1939 Doane ..................... F21V 21/03
248/343
(Continued)

FOREIGN PATENT DOCUMENTS

DE           3100819 A1    7/1982
DE   10 2012 001 197 A1    7/2013
(Continued)

*Primary Examiner* — Christopher Garft
(74) *Attorney, Agent, or Firm* — Seed IP Law Group LLP

(57) ABSTRACT

A mounting device for mounting a stand device under a ceiling in an operating room incorporates a mounting apparatus extending in the longitudinal direction along a mounting axis configured to bear a connection component of the stand device, in particular a spindle; and a ceiling flange configured to mount the mounting apparatus under the ceiling and to support the stand device on the ceiling; wherein the ceiling flange is mountable in different mounting positions along the mounting axis relative to the mounting apparatus on the mounting apparatus in a way that the mounting device is configured to hold the stand device in a height variable manner in different, in particular predefined, height positions. The invention further relates to a mounting system including such a mounting device.

22 Claims, 8 Drawing Sheets

(51) Int. Cl.
*F16M 13/02* (2006.01)
*F16M 11/20* (2006.01)

(58) Field of Classification Search
CPC ...... F16M 11/26; F16M 11/04; F16M 11/046; F16M 11/28; F16M 11/06; F16M 11/08; F16B 7/105; F16B 7/10; F16B 7/14; F21V 21/22
See application file for complete search history.

(56) References Cited

U.S. PATENT DOCUMENTS

| | | | | |
|---|---|---|---|---|
| 2,692,745 A | * | 10/1954 | Barrett | H01Q 1/1242 |
| | | | | 248/541 |
| 2,795,859 A | | 6/1957 | Buschbach | |
| 2,916,249 A | * | 12/1959 | Wolar | F21V 21/00 |
| | | | | 248/327 |
| 3,814,023 A | | 6/1974 | Stantial | |
| 4,673,154 A | | 6/1987 | Karapita | |
| 4,684,097 A | * | 8/1987 | Cox | E04B 1/34336 |
| | | | | 248/354.3 |
| 4,687,167 A | | 8/1987 | Skalka et al. | |
| 4,738,369 A | | 4/1988 | Desjardins | |
| 4,803,819 A | * | 2/1989 | Kelsey | B29C 70/521 |
| | | | | 174/45 R |
| 4,840,278 A | | 6/1989 | Gelinas | |
| 4,901,967 A | | 2/1990 | Petre | |
| 4,948,083 A | | 8/1990 | McNaney, Jr. et al. | |
| 5,014,693 A | * | 5/1991 | Wright, II | F16M 11/08 |
| | | | | 128/203.12 |
| 5,505,420 A | * | 4/1996 | Brown | F04D 25/088 |
| | | | | 248/343 |
| 6,095,468 A | | 8/2000 | Chirico et al. | |
| 6,443,406 B1 | * | 9/2002 | Frank | F16B 12/44 |
| | | | | 248/125.8 |
| 6,443,596 B1 | | 9/2002 | Bulko et al. | |
| 6,639,623 B2 | | 10/2003 | Howell et al. | |
| 7,097,145 B2 | | 8/2006 | Turner | |
| 7,770,860 B1 | | 8/2010 | Culpepper et al. | |
| 7,823,347 B1 | * | 11/2010 | Blinn | E04C 3/08 |
| | | | | 52/244 |
| 8,197,154 B2 | | 6/2012 | Broering et al. | |
| 8,276,867 B2 | | 10/2012 | Hung | |
| 8,602,367 B2 | | 12/2013 | Wang et al. | |
| 8,876,075 B2 | | 11/2014 | Diez | |
| 9,022,339 B2 | | 5/2015 | Borg et al. | |
| 9,033,106 B2 | * | 5/2015 | Blinn | E04G 21/3266 |
| | | | | 182/139 |
| 9,239,127 B2 | | 1/2016 | Krönung | |
| 9,528,285 B2 | * | 12/2016 | Blinn | E04G 21/3266 |
| 9,999,480 B2 | | 6/2018 | Oginski et al. | |
| 2003/0052245 A1 | | 3/2003 | McKeown et al. | |
| 2003/0141426 A1 | | 7/2003 | Wagner et al. | |
| 2003/0173482 A1 | | 9/2003 | Kuhn | |
| 2008/0116333 A1 | * | 5/2008 | Chang | G09F 7/20 |
| | | | | 248/200.1 |
| 2009/0213596 A1 | | 8/2009 | Gull et al. | |
| 2013/0168626 A1 | * | 7/2013 | Blinn | E04G 21/3233 |
| | | | | 256/31 |
| 2013/0187022 A1 | | 7/2013 | Duportal et al. | |
| 2015/0316200 A1 | | 11/2015 | Hoshi et al. | |

FOREIGN PATENT DOCUMENTS

| | | |
|---|---|---|
| GB | 2489608 A | 10/2012 |
| WO | 94/27549 A1 | 12/1994 |

\* cited by examiner

MOUNTING DEVICE FOR A STAND DEVICE AND MOUNTING SYSTEM INCLUDING THE MOUNTING DEVICE

BACKGROUND

Technical Field

The present invention relates to a mounting device for mounting a stand device under a ceiling in an operating room, comprising: a mounting apparatus extending in the longitudinal direction along a mounting axis configured for holding a connection component of the stand device, in particular a spindle; and a ceiling flange arranged for mounting the mounting apparatus under the ceiling and for supporting the stand device on the ceiling. In particular, the present invention relates to a mounting device including the single features of claim 1, and a mounting system including single features of the independent system claim.

Description of the Related Art

Stands, in particular, ceiling stands, as for example, ceiling supply units, monitor supports, or so-called spring arms or central axes, usually comprise one or more carriers arranged rigidly or in a way to be adjustable in height regarding a vertical position, by means of which an attached medical device may be moved and positioned, for example, in an operating room, in particular, also in an intensive care unit. At the stands usually supply units are attached, on which medical devices are arranged, for example, which will be supplied with the required media during a surgery, for example. The carriers define a radius of action of the medical device within which the medical device can be positioned. The carriers are usually rotatable around at least one rotatable connection, in particular a rotary joint. The carriers are optionally arranged to be vertically adjustable and/or vertically pivotable around an at least approximately horizontally aligned axis.

Usually the stand is mounted on a ceiling or adjacent to a subceiling of the operating room. Here, the subceiling is used to mount cables, for example, but not to support the stand. Hereto the stand comprises a ceiling tube, for example. Here, often the height position of the stand has to be aligned in relation to the ceiling. The height position of the stand relative to a mounting point on the ceiling may define the position of a medical device supported by the stand. Often the exact height position of the subceiling is unknown. However, the stand has to be mounted in an exactly defined height.

In order to mount the stand, mounting devices that include disks shrink-fitted on a spindle of the stand, for example, may be used. The shrink-fitted disks may be screwed to the ceiling tube.

For an adjustment in height, vertically adjustable ceiling tubes may be used. Here, for example a clamp connection with annular wedge segments may ensure a variable height position by a force-fit connection. An additionally required form-fitting bolt securement may ensure a relative position of the ceiling tube on a ceiling flange. Then, the bore required for the bolt at a predefined position has to be made individually at the correct position afterwards during mounting. Here, the ceiling tube may have to be pushed to a higher position than the ceiling flange. In case there is not enough space above the ceiling flange, the ceiling tube may have to be shortened, if required.

Also, devices are known for which a ceiling flange, on which the spindle is fixedly preassembled, is mounted by using threaded rods and optionally also spacer tubes on a so-called interface plate, which in turn is mounted on a so-called ceiling plate, also by using threaded rods and spacer tubes. By using threaded rods an adjustment in height and also an alignment may be performed.

BRIEF SUMMARY

It is an object of the present invention to provide a mounting device by means of which the stand device may be mounted on a ceiling in a predefined height position without having to perform expensive design changes or adaptions of the mounting device. In particular, the object is to provide a mounting device by means of which the adjustment or readjustment of the height position may be performed easily, in particular manually. Preferably, the mounting device also has a high bearing capacity and is suited to accommodate and transfer high weights. Preferably, the mounting device has a simple design and can be manufactured inexpensively.

Said object is achieved by a mounting device for mounting a stand device under a ceiling in the operating room, comprising: a mounting apparatus extending in a longitudinal direction along a mounting axis configured to hold a connection component of the stand device, in particular a spindle; and a ceiling flange configured to mount the mounting apparatus under the ceiling and to support the stand device on the ceiling; wherein the ceiling flange is mountable in different mounting positions along the mounting axis relative to the mounting apparatus on the mounting apparatus in a way that the mounting device is configured to support the stand device in a height variable manner, in different, in particular predefined, height positions. The mounting device comprises a ceiling flange and a mounting apparatus which are matched in design to each other in such a manner that the ceiling flange and the mounting apparatus may be coupled to each other at different coupling points/fasting points in different relative positions. This way, a height position may be defined according to the room situation or the size of the stand device.

The ceiling flange may be mountable in at least two predefined mounting positions, in particular height positions, on the mounting apparatus. The mounting apparatus may thus be adjusted and screwed together in a well accessible position, for example on the floor, and then be mounted on the ceiling. It is advantageous to measure the height of the ceiling or the subceiling in advance in order to be able to adjust the suitable height position.

In a mounted state, the longitudinal direction corresponds preferably to a height direction, in particular a vertical direction.

A stand device is thus preferably a device for holding, fixing a position, and/or displacing at least one medical device that for medical purposes may be firmly mounted or positioned on a wall (in a wall bearing), or on a ceiling, or also on a floor of an operating room, or any other room; for example, a ceiling stand. The stand device may thus not be moved in a completely unrestricted way in the operating room, but may only be moved within a certain radius of action, in particular, relative to a fastening point or mounting point on a ceiling or a wall of the operating room. The stand device may be configured as a ceiling supply unit mounted on a ceiling, and include one or more supply units supported adjustably in position on one or two carrier arms. The stand device may also be adapted as a monitor support. The stand device may also be adapted as a so-called spring arm, in particular one that is mounted on a wall and includes a light, for example. The stand device may also be adapted as a so-called central axis mounted, in particular on a ceiling, and comprise a plurality of carrier systems, each having at least one carrier on which a monitor or a light is mounted, for example. Preferably, the stand device has at least two support arms.

A medical device is preferably a supply unit by means of which the means for treating a patient and/or instruments for a surgeon and/or light, clean air, or other media required in the operating room can be provided. The medical device preferably includes some kind of control panel and/or some kind of display device for graphically displaying patient data, for example.

Here, the mounting apparatus is preferably a device by means of which the stand device may be mounted on a room ceiling and by means of which a weight or force of inertia applied by the stand device may be transferred to a ceiling, in particular by using a ceiling flange. The mounting apparatus may be mounted on a ceiling flange by one or more supports.

Here, a connection component is preferably a component by means of which single carriers of the stand device may be connected to the mounting device and preferably also to one another. At a stand device adapted as a so-called central axis, the connection component may be formed as a centrally arranged spindle which supports several carriers or carrier arms.

An operating room may also be an examination room or an intensive care unit or a room for performing medical treatments or therapies.

According to an exemplary embodiment the mounting apparatus comprises at least one fastening portion including a plurality of fastening means, in particular being formed identically, which are spaced in the longitudinal direction. The fasting means enable a plurality of different relative positions of the mounting apparatus in relation to the ceiling flange. Preferably, the fasting means are aligned in a transverse or orthogonal direction to the longitudinal direction.

According to an exemplary embodiment the at least one fastening portion is arranged on an outside, in particular an outer contour or outer lateral surface of the mounting apparatus. This allows to ensure a good accessibility. The fasting means of the mounting apparatus are arranged in the longitudinal direction to one another, preferably equally spaced. Preferably, the respective fastening portion is formed as a perforated bar.

According to an exemplary embodiment the at least one fastening portion is arranged on a crosspiece protruding in a radial direction on an outside or outer contour of the mounting apparatus, or forms said crosspiece. This arrangement also enables to access the fastening portion from both sides, for example. The crosspiece may also be described as tongue, or may also be formed as tongue.

According to an exemplary embodiment the at least one fastening portion extends in the longitudinal direction along the complete length of the mounting apparatus, respectively. This enables a very flexible adjustment in height. The complete length of the mounting apparatus may be used to adjust individual height positions.

Preferably, the fasting portion of the mounting apparatus comprises at least one, preferably two, radially aligned planar radial flanks (in particular opposite side faces) which preferably are provided along the complete fastening portion. The ceiling flange or a support may optionally be arranged on one or more of these radial flanks and may be shifted thereon in the longitudinal direction. Optionally the ceiling flange or support may also enclose two opposite radial flanks of the respective fastening portion of the mounting apparatus. The mounting apparatus may be exactly positioned in a predetermined position in relation to the ceiling flange by using the radial flanks.

Preferably, the mounting apparatus is adapted as tube, wherein at least 2 or 3 fastening portions adapted as crosspieces are arranged on an outer contour of the mounting apparatus, preferably in the same distance to each other in the circumferential direction. This enables a stable fastening on a fastening point (positioned far outside) that is advantageous regarding torques, respectively, or with a special symmetric force distribution. Preferably, 3 fastening portions are provided, which are arranged in a distance corresponding to a circumferential angle of 120° to each other on the outer contour, respectively.

According to an exemplary embodiment the ceiling flange comprises a passage which preferably has an inner diameter which is larger than or larger equal than an outer diameter of the mounting apparatus. This enables a passing through/guiding through of the mounting apparatus through the ceiling flange. This way a plurality of relative height positions/mounting positions may be provided. Here, the mounting apparatus has not to be shortened, even in case the ceiling flange has to be fastened comparatively far below, in particular on a lower end of the mounting apparatus to enable a particularly high position of the stand device. Thus, a comparatively high height position of the stand device may be adjusted in a simple way, in particular without having to change any components.

The passage preferably includes an inner contour which is formed to correspond geometrically to an outer contour of the mounting apparatus. Hereby a form-fitting rotational lock can also be provided by means of the ceiling flange, for example. Preferably, the passage comprises recesses aligned in a radial direction that are formed to correspond geometrically to crosspieces of the mounting apparatus. The recesses may facilitate the positioning and guiding of the mounting apparatus, in particular during mounting of angular, separate supports on the ceiling flange and on the mounting apparatus.

The inner contour preferably forms at least one radial groove, which is formed to correspond geometrically to a fastening portion, in particular a crosspiece of the mounting apparatus. Thereby the mounting apparatus may be supported on the ceiling flange without noticeable circumferential backlash (disregarding a circumferential backlash caused by manufacturing tolerances).

According to an exemplary embodiment the ceiling flange comprises a planar lower front face where the mounting apparatus or a support may abut, wherein the ceiling flange is preferably adapted as flange plate. Thus, a contact surface may be provided for force transmission and for a predefinable positioning.

According to an exemplary embodiment the ceiling flange comprises a plurality of fastening means, in particular internally threaded bores or passage openings adapted to fasten the mounting apparatus on the ceiling flange, and which are preferably aligned in the longitudinal direction. This facilitates mounting. Fasting means or fastening elements engaging therewith may be aligned in the prevailing force flux direction. Preferably, the fasting means are formed as through-bores. Through-holes allow to insert screws from above.

According to an exemplary embodiment the mounting apparatus comprises at least one support by means of which the mounting apparatus is coupable in different relative positions on the ceiling flange, wherein the support comprises a fastening portion which is formed to correspond geometrically to a fastening portion of the mounting apparatus. Here the support is configured to couple the ceiling flange with the mounting apparatus and to transfer a load, in particular weight, applied by the stand device from the mounting apparatus to the ceiling flange.

According to an exemplary embodiment the support is provided as individual part separate from the ceiling flange and separate from the mounting apparatus. Optionally the support may be preassembled on the ceiling flange or may be formed integrally by a portion of the ceiling flange protruding in the axial longitudinal direction. According to a variant support and ceiling flange are adapted as cast part.

According to an exemplary embodiment the support comprises at least one fastening means which is arranged and/or formed to correspond geometrically to the fastening means of the mounting apparatus. Thus, the support and the mounting apparatus may be positioned in a predefined arrangement relative to one another. Fastening elements, in particular screws, may be mounted on the fastening means. According to a variant the mounting apparatus may be hold by means of the support without fasting means in a form-fitting and/or force-fitting way. In particular, this may be ensured by the fact, that the support may engage with the mounting apparatus in an elastically biased way and may support the mounting apparatus (its self-weight). An additional securement by bolts is not required. This is advantageous during mounting, as first the support may be mounted on the ceiling flange, and then the mounting apparatus may be positioned on the support in a desired height position in a way that the respective fastening means are disposed in alignment to each another. Fasting elements may then be attached/mounted without having to hold to the mounting apparatus.

Preferably, the at least one fastening portion of the mounting apparatus has an extension in the longitudinal direction larger than the support. This allows for an axial displacement of the support along the fastening portion. Preferably, the support comprises an extension in the longitudinal direction which is more than double than the distance of two fastening means of the mounting apparatus arranged adjacently in the longitudinal direction. This allows to ensure that the mounting apparatus may be positioned relative to the ceiling flange in different distances without having to shorten the mounting apparatus or guide it through the ceiling flange. Nonetheless the mounting apparatus may be guided through the ceiling flange and protrude from the top of the ceiling flange. Preferably, the support has an extension in the longitudinal direction which is more than triple than the distance of two fastening means of the mounting apparatus to one another. This way a plurality of relative height positions may be set.

According to a variant the support is a L-shaped bracket and includes a planar longitudinal face and a planar front face by means of which the support may abut on the ceiling flange and on the mounting apparatus, respectively.

According to an exemplary embodiment the support comprises a cavity, in particular a radial cavity aligned in the radial direction, which is formed to correspond geometrically to the fastening portion of the mounting apparatus, thus the support is configured to enclose the fastening portion in the radial direction. This way the mounting apparatus may be guided in the support in the longitudinal direction and may be centered by one or more supports.

According to a variant the support comprises two opposite jaws which form a radial flank (side face), respectively, surrounding the cavity in the circumferential direction where the fastening portion of the mounting apparatus abuts. Here the support may also be formed as bracket.

Preferably, the support comprises a centering face surrounding the cavity in the radial direction, which is formed to correspond geometrically to a peripheral surface portion of the fastening portion positioned radially outside. This enables a centering of the mounting apparatus by using one or more supports relative to the ceiling flange.

Preferably, the support comprises a corrugation that is disposed in a way that the support may be deformable in order to facilitate mounting of the mounting apparatus on the corrugation.

According to an exemplary embodiment the mounting apparatus is a tube-like continuous casting part, in particular made from aluminium, wherein the mounting apparatus is preferably made of one piece. The term aluminium may also comprise aluminium alloys. Preferably, the aluminium alloy AlMgSi0.5 is used. This configuration enables high stability on the one hand, and cost-efficient manufacturing on the other hand. Here the axial extension around the mounting axis may be selected largely arbitrarily, depending on the operating conditions and the mounting position. Preferably, a support to connect the mounting apparatus with a ceiling flange is formed as a continuous cast part.

According to a variant no supports are provided. The mounting apparatus preferably comprises threaded channels, in particular at the rim, by means of which the mounting apparatus may be mounted directly on the/a flange plate. Thus, a very cost-efficient variant may be provided. The number of components or parts is reduced. The mounting may further be simplified, in particular in applications that require no particularly high flexibility regarding an adjustment in height.

According to an exemplary embodiment the mounting apparatus comprises at least one fastening portion with a plurality of fastening means that are spaced to one another in the longitudinal direction, wherein the at least one fastening portion is arranged on an outside of the mounting apparatus and is formed as a radially protruding crosspiece, wherein the at least one fastening portion extends along the complete length of the mounting apparatus, respectively, wherein the mounting device comprises at least one support by means of which the mounting apparatus is coupable to the ceiling flange in different relative positions, wherein the support comprises a fastening portion which is formed to correspond geometrically to a fasting portion of the mounting apparatus, wherein the support comprises at least one fastening means which is arranged and/or formed to correspond geometrically to fastening means of the mounting apparatus, wherein the ceiling flange comprises a lower front face where the support may abut, wherein the ceiling flange comprises a plurality of fastening means aligned in the longitudinal direction and configured to mount the support on the ceiling flange. By means of this configuration a plurality of the advantages of the present invention may be realized.

According to an exemplary embodiment the mounting apparatus includes two mating faces in different sizes which are formed to correspond to the mating faces of the connection component and are configured to facilitate the mounting and to enable a two-point support of the connection component. This is advantageous regarding a secure mounting and a stressable support.

According to a preferred embodiment of the mounting device the mounting apparatus is adapted tube-like and the fastening portions are formed as crosspieces protruding radially from the outer contour of the mounting apparatus, wherein at least 2, preferably at least 3, fastening portions are provided on the mounting apparatus which work together with a number of supports on the ceiling flange. The fastening elements required for a connection of ceiling flange and mounting apparatus with the spindle supported thereon do thus not cross or penetrate the tube-like portion of the mounting apparatus, but only the crosspieces arranged radially outside, thus the tube-like portion of the mounting apparatus is not weakened. This way, an extremely robust mounting device may be provided which is able to accommodate high traction forces.

The object described above is also achieved by a mounting system including a mounting device according to the invention, wherein the mounting system further comprises: at least one fastening element, in particular a screw, for mounting the ceiling flange on the mounting apparatus or on a support coupled with the mounting apparatus and/or at least one fastening element, in particular a screw, to mount the at least one support on the mounting apparatus. Such a system provides a high degree of flexibility during mounting or selection of a certain height position.

According to an exemplary embodiment the mounting system further comprises an adjustment apparatus to arrange a connection component of the stand device in a predefined position relative to the mounting apparatus, wherein the mounting apparatus forms a rotational coupling that is adjustable around the mounting axis to support the connection component on the mounting apparatus. This way, in addition to an adjustable height position also an adjustment or readjustment of the relative rotational position of the spindle in relation to the mounting device may be performed in a simple way, as will be described in the following in detail.

A stand device including a mounting system according to the invention preferably comprises a connection component adapted as a spindle, which is supported on or fastened to the mounting apparatus in an axially locked way. Preferably, the spindle is supported rotatably on the mounting apparatus. In the following, further variants or features are described regarding a spindle that is rotatably supported, which may be achieved advantageously by the mounting device of the invention.

According to a variant the mounting device is configured to displace a medical device in the operating room, wherein the mounting apparatus comprises a cavity aligned in the longitudinal direction to accommodate a rotatably supportable connection component of the stand device, and wherein the mounting device further comprises: an adjustment apparatus for arranging the connection component in a predefined position in relation to the mounting apparatus, wherein the mounting device forms a rotational coupling which is adjustable about the mounting axis to support the connection component on the mounting apparatus. This way, in addition to an adjustable height position an adjustment or readjustment of the relative rotational position in relation to the mounting device is also simple. The radius of action of the stand may be defined in a simple way. Preferably, the rotational coupling may be adjusted without having to disassemble any components of the mounting device or stand device except from a cover.

Preferably, in a first state, the mounting apparatus is configured to support the connection component in a rotatable and axially fixed manner, and in a second state to support the connection component in a rotatably fixed and axially fixed manner, in particular when coupled with the adjustment apparatus. This enables the adjustment of predefined rotation angle positions by using the adjustment apparatus.

An adjustment apparatus preferably is a device by means of which a determined relative position of the connection component may be adjusted or set in relation to the mounting apparatus. By means of the adjustment apparatus individual relative positions may be predetermined. The adjustment apparatus is preferably supported on the connection component in a rotatably fixed manner.

Preferably, a rotational coupling is a connection by means of which a coupling may be ensured in a predetermined rotational position, wherein a relative rotational movement is possible either in steps or continuously.

According to a variant the adjustable rotational coupling is formed by the adjustment apparatus and the mounting apparatus, wherein the adjustment apparatus may be positioned in a predetermined rotational position about the mounting axis in relation to the mounting apparatus and is supportable in a rotationally fixed manner. This way, an adjustment may be performed by rotating the adjustment apparatus in relation to the mounting apparatus. The adjustment apparatus is configured to support the connection component in a rotatably fixed manner on the mounting apparatus.

According to a variant the adjustment apparatus is formed as an individual component of the mounting device separate from the connection component and separate from the mounting apparatus. By configuring the adjustment apparatus as an individual unit separate from the spindle a coupling may be provided by means of which the position of the spindle in relation to the mounting apparatus may be adjusted in a flexible and simple way. Preferably the mounting device is coupled to the connection component in a form-fitting manner, in particular in different axial positions. This kind of interface enables, for example, the arrangement of different numbers of carriers or carriers with different dimensions without having to change the interface design.

The cavity is formed to correspond geometrically to the connection component and provides a rotary bearing to the connection component. This way, the connection component in the mounting apparatus may be rotated in order to adjust the rotational position.

Preferably, the mounting apparatus and the adjustment apparatus are arranged axially in series to one another and overlap the connection component, respectively.

According to a variant the adjustment apparatus includes a rotational stop, in particular a groove or spring, which is formed to correspond geometrically to a rotational stop, in particular groove or spring, arranged on the connection component. Hereby a rotation of the adjustment apparatus may cause a rotation of the spindle and vice versa. Thus, defining the rotational position of the adjustment apparatus relative to the mounting apparatus also allows to directly adjust the rotational position of the spindle, for example in the operating room. Preferably, the groove extends at least approximately along a longitudinal axis direction of the connection component. The rotational stop may optionally be formed as a form-fitting coupling, for example a sprocket, any steps or crosspieces that radially engage with one another. The rotational stop may also be used for centering.

Preferably, the mounting apparatus is configured to provide a securement against rotation, in particular by using an axially arranged passage, and also to provide a securement of the connection component in the axial direction, in particular by means of at least one radially arranged passage. This way, readjusting or adjusting of the rotational coupling may be performed smoothly without the need for any other tools or support devices, even if the stand device has a significant own mass, for example in cases where a complete supply unit is fastened to the stand device.

According to a variant the adjustment apparatus comprises a plurality of coupling points, in particular openings or passages, to define one of a plurality of rotational positions of the rotational coupling, respectively, which are preferably arranged on a pitch circle, wherein the adjustment apparatus preferably has an annular geometry or is adapted as an annular disk (flat ring). Preferably, the coupling points are accessible via an upper side of the adjustment apparatus, respectively. Preferably, the pitch circle is larger than a diameter of the cavity ensuring a good access from outside. Preferably, the coupling points are arranged on the adjustment apparatus as far as possible radially outwards. Thereby an adjustment is easy, even when the adjustment apparatus is arranged under a ceiling and is difficult to access. Preferably, the coupling points are accessible via a front face of the adjustment apparatus. Preferably, the openings or passages are aligned axially, in particular parallel to the mounting axis.

The adjustment apparatus preferably includes an outer diameter that is larger than or equal to further components of the mounting device. This way, the adjustment apparatus may provide an interface at a peripheral surface or an outer rim, in particular mounting slots, where a cover or enclosure of the mounting device may be mounted. Fastening a cover on the adjustment apparatus provides the advantage that the cover is easy to remove and that access to the rotational coupling is easy.

The adjustment apparatus may comprise an annular support surface that is formed to correspond geometrically to an annular support surface of the connection component. Thus, the connection component can be exactly coupled with the adjustment apparatus. The support surface may act as a stop for a corresponding step of the connection component.

According to a variant the adjustment apparatus includes a passage with an inner diameter smaller than the diameter of the cavity or smaller than the inner diameter of an inner lateral surface of the mounting apparatus. Thereby the connection component may abut on a step of the connection component on the adjustment apparatus.

According to a variant the mounting apparatus comprises a planar lower front face where the adjustment apparatus may abut in a predefined axial position. Thereby the adjustment apparatus may be aligned exactly in relation to the mounting apparatus. Thus, a rotational lock element may be arranged in different positions without jamming, in particular manually.

According to a variant the mounting apparatus comprises at least one fastening portion with a plurality of fastening means, in particular openings or bores, wherein the fastening means define different axial mounting positions. Thereby a particular height position of the stand device in relation to a ceiling or ceiling flange can be easily adjusted.

Preferably, the mounting apparatus comprises 15 to 30, preferably 20 to 25 openings, thus a relative rotational position of the spindle in relation to the mounting apparatus may be adjusted in comparatively small angular steps, for example in steps of 15°. Such adjustments of the relative rotational position are particularly advantageous regarding stops or rotational locks limiting rotational movements of the stand device. Thus, the radius of action of the stand device may be flexibly adjusted to position the medical device.

According to a variant the mounting apparatus comprises a plurality of threaded bores to accommodate fastening elements that can be arranged in a longitudinal direction/vertical direction, wherein the threaded bores are arranged on the same pitch circle as corresponding coupling points/openings of the adjustment apparatus. The threaded bores are preferably arranged on a lower front face of the mounting apparatus and extend at least approximately in the longitudinal direction. This enables a simple mounting and a simple readjustment. Preferably, 3 to 5 threaded bores are provided that are accessible from a lower side in a mounted state of the mounting apparatus, thus fastening elements may be plugged-in and fastened, in particular screwed, from below in an axial longitudinal direction. A technician may thus mount any fastening elements under the mounting apparatus, basically without having to change his/her position. Screwing in the radial direction is not required. This also enables the technician to work from a lower height, making the mounting procedure less dangerous by reducing the risk of a fall by the technician, for example. In addition, a visual examination of the fastening elements to ensure a correct positioning may be performed easily. Thus, a pressure or force that may be applied manually in the mounting direction, that is in the longitudinal direction, may more easily applied exactly in the longitudinal direction.

According to a variant the at least one fastening portion is formed on an outer lateral surface by a crosspiece protruding in the radial direction, wherein the mounting apparatus preferably comprises at least 3 fastening portions that are arranged in a star shape, in particular spaced equally to one another in a peripheral direction. This way a load (in particular a weight or torque) may be transferred to a force engagement point positioned further outwards. In particular, with several fastening portions being symmetrically distributed around the circumference of the mounting apparatus, a force may be transferred to advantageous force engagement points in a uniform way. Also in case the adjustment apparatus has to be fastened to the mounting apparatus, a predefined rotational position may be set in a comparatively exact manner or in especially small rotational steps or rotation angles, in particular independent of a diameter of the spindle and largely independent of the loads to be transferred.

Preferably, the fastening portions are circumferentially arranged on the outer lateral surface, in particular equally spaced in the peripheral direction. This facilitates an adjustment regarding a plurality of different rotation angle positions.

According to a variant the mounting apparatus includes a retainer, in particular tube-like, for a rotational lock element, wherein the retainer is preferably arranged on an outside, in particular an outer lateral surface, of the mounting apparatus, or constitutes the outer lateral surface at least in sections. This allows for removal or insertion of a rotational lock element in a simple way. Preferably, the retainer comprises a through-bore that extends down to the lower front face of the mounting apparatus. A retainer configured in such a way may also be denoted as a locking tube.

Preferably, the retainer is formed to arrange a rotational lock element aligned in the axial direction, in particular a bolt connection in the axial direction. Preferably, the retainer comprises a lower (in particular tube-like) retainer portion with an axial extension smaller than a length of the rotational lock element.

According to a variant the retainer comprises an access, in particular an access radially from outside, wherein the access is preferably formed as cutout. This facilitates a manual adjustment. Preferably, the access comprises an axial extension that is larger than a length of a rotational lock element and larger than an axial extension of a lower retainer portion.

The access preferably comprises an upper access area where a rotational lock element may abut. On the upper access area a bolt including a rim/head/step may be supported in a way that the rotational coupling may be easily adjusted manually. The bolt may be plugged into the retainer and may only be secured by gravitational force. This way a technician has only to perform a plug-in movement, which is executed in very short time. A rotational movement or screwing is not required. This is especially advantageous for positions directly underneath a ceiling that are difficult to access. The rotational lock element may be removed manually and re-mounted in a simple way, in particular without using tools. This provides advantages, especially for hard to access mounting points of the stand device, last but not least, as a technician has both hands free.

According to a variant the mounting device comprises an axial lock by means of which the connection component may be supported on the mounting apparatus in a predefined axial position, in particular rotatable in relation to the mounting apparatus. The axial lock may facilitate mounting and also readjustment. The stand may be locked using an axial lock, in particular during the alignment of the rotational position, or during fastening of individual fastening elements. The mounting device may also reduce the risk of jamming within the mounting apparatus. By using only three main components, the mounting device may thus provide an easily adjustable rotational coupling. Here the coupling consists of three main components, that is the mounting apparatus, the adjustment apparatus or the flat ring, and the axial lock.

Preferably, the axial lock forms an axially fixed rotary bearing for the connection component together with the cavity, that is, a bearing enabling a rotation in a predefined axial position. The axially fixed rotary bearing provides a degree of freedom of movement around the mounting axis and prevents a movement along the mounting axis.

According to a variant the axial lock is configured to be mounted permanently and to ensure an axial lock of the connection component in various or any mounting situations.

According to a variant the mounting apparatus is configured to fasten and rotatably support the connection component in a predefined relative axial position, wherein a chamfer, edge or milled recess is provided at an inner lateral surface of the mounting apparatus surrounding the cavity. This way an axially fixed rotary bearing may be formed by simple design components that may be easily mounted during mounting of the stand device.

According to a variant the axial lock comprises a passage arranged tangentially on the mounting apparatus that passes through an outer contour or outer lateral surface of the mounting apparatus, preferably at two points, and that intersects an/the inner lateral surface of the mounting apparatus. The passage (in particular a bore or cutout) may be arranged as a secant in relation to the outer lateral surface of the mounting apparatus. In the passage a securing element (in particular a bolt or latch) may be inserted tangentially to the connection component which may engage with a groove of the connection component and axially secure the connection component in the mounting apparatus. Preferably said securing element may be arranged tangentially to the mounting apparatus and is formed to correspond geometrically to the passage.

The tangentially aligned passage may intersect an inner contour, in particular an inner lateral surface of the cavity in a way that the latch is arranged further inwards than the inner lateral surface. For example, the latch protrudes about half of its diameter further inwards than the inner lateral surface. A passage arranged as secant has the advantage of providing a comparatively long latch engagement portion with the connection component as compared to a radially aligned securing bolt. Thus, the latch is arranged tangentially to the connection component, and engages with a peripheral side of the connection component tangentially in sections in the connection component. In addition, this kind of axial lock has the advantage that the axial lock does not need not to be removed, in particular when rotating the connection component during mounting. Here friction can be kept relatively low during a relative rotation of the connection component within the cavity. A rotation may be performed in a simple way, even for long carrier arms or high weights or torques, in particular by engaging with a recess on the lower side of the adjustment apparatus. The axial lock or the tangential latch may remain in the tangential position.

According to a variant spacers may be provided between the adjustment apparatus and the lower front face of the mounting apparatus to allow an adjustment of the height position of the connection component in relation to the mounting apparatus. In addition, a plurality of tangential passages may be provided one above another in the mounting apparatus, respectively, to accommodate a securing element for an axial lock. Thereby an adjustment in height may be performed easily without having to use spacers.

Preferably, a support surface is formed on the passage that is configured to transfer a weight applied from the connection component to the mounting apparatus. According to a variant, the support surface is U-shaped. This way the passages may be manufactured in a cost-efficient way, in particular by milling. Furthermore, notch stresses may be reduced to a minimum in the mounting apparatus and also in the connection component. Preferably, the radius of the passage on the upper side is smaller than the radius on the lower side. This allows to specify how the respective locking element has to be arranged in the passage. A risk of faulty mounting may thus be reduced.

According to a variant the axial lock comprises at least one securing element, in particular a latch, that is adapted and configured to transfer the weight of the stand device from the connection component to the mounting apparatus. Thus, the rotational position may be readjusted without having to disassemble any components of the stand device, in particular any components of the central axis. During adjustment of the rotational position, the complete stand device may be supported on the axial lock. In other words, the axial lock is configured to form a rotary bearing for the stand device. This facilitates readjustment significantly due to the fact that only the adjustment apparatus has to be disassembled and then fastened again in a readjusted rotational position.

According to a variant the passage and the retainer for a rotational lock element are arranged on the same peripheral surface portion of the mounting apparatus, in particular in a way to be manually accessible from the same side. This facilitates the adjustment and mounting of the device. Thus, a securement of the rotational lock element and the securing elements for an axial lock may be provided by using spring connectors, namely from the same side or on the same peripheral surface portion. Last but not least, this is advantageous for mounting.

The mounting system may also comprise the connection component adapted as a spindle and a rotational lock element and at least one securing element as axial lock, wherein the spindle is provided with a peripheral groove or a peripheral step that is formed to correspond geometrically to the securing element. In other words, the mounting system comprises different securing elements for axial locking and for rotational locking, respectively. Preferably, both types of securing elements are mountable on the same peripheral position of the mounting apparatus. Here a single securing element may be provided as an axial lock. Preferably, two securing elements are provided as an axial lock. Optionally, also three securing elements may be provided as an axial lock.

Preferably, the groove is provided circumferentially and extends orthogonal to a longitudinal direction. A peripheral groove provides the advantage that the bolt of the axial lock may engage with the spindle independent of the respective rotational position. In addition, the spindle may be easily rotated relative to the mounting apparatus, even in cases of a load acting on the axial lock in the axial direction. This facilitates the readjustment or changing of the rotational position.

Preferably, the groove is spaced apart from the front face or a front face stop of the spindle, which corresponds to a distance of the bore to a counter-stop in the cavity when seen in the longitudinal direction. This facilitates mounting, in particular as a front face of the spindle may abut on a/the counter-stop of the mounting apparatus in such a way that the spindle is arranged in the correct axial position in order to provide an axial lock. In this axial position the bolt may engage tangentially with an outer lateral surface of the spindle. It is not necessary to readjust the axial position. The counter-stop of the mounting apparatus may also be provided as bottom of the cavity or a peripheral annular or disk-shaped counter-stop at the bottom of the cavity.

According to a variant a step is formed on the spindle that is overlapped by the adjustment apparatus in a radial direction. This enables a support of the spindle by means of the adjustment apparatus. Said step may enable to fix the position of the adjustment apparatus together with one or more carrier arms by using a lower shaft nut securing the carrier arms. In particular, mounting may be facilitated by the fact that the adjustment apparatus is secured before inserting the spindle in the mounting apparatus, in particular regarding a slipping downwards.

As a first mounting step, the mounting apparatus may be mounted on the ceiling. Then the spindle may be plugged into the cavity of the mounting apparatus from below. Preferably, the adjustment apparatus is already arranged on the spindle and may be fastened to the mounting apparatus. This way the spindle may be positioned on the mounting apparatus in the axial longitudinal direction. Optionally the spindle may also be secured by an axial lock on the mounting apparatus before fastening the adjustment apparatus, thus the adjustment apparatus may be positioned in a predetermined rotational position without having to accommodate a weight of the spindle via the adjustment apparatus at the same time. This facilitates mounting or also a later adjustment of a predetermined rotational position.

According to a variant an outer diameter of the step of the spindle is larger than an inner diameter of a passage of the adjustment apparatus. In this configuration the spindle is optionally supportable by using the adjustment apparatus in the axial direction. The radial overlapping is preferably at least 1 mm.

According to a variant, a rotational stop is arranged below the step, in particular an (adjusting) spring, that is preferably aligned in the longitudinal direction. The rotational stop is formed to correspond geometrically to a rotational lock of the adjustment apparatus. The rotational stop may, for example be an adjusting spring mounted in a corresponding groove of the spindle, or a moulded spring.

According to a variant the mounting system comprises a rotational lock element adapted as bolt engaging in the axial direction and two securing elements adapted as latches engaging tangentially, wherein the bolt and the latches are arranged adjacent to an access provided in a retainer for the rotational lock element. Said arrangement facilitates adjusting and mounting.

The object described above is also achieved by a support for a stand device arrangeable in an operating room, wherein the support is configured to connect a connection component of the stand device with a ceiling flange, wherein the support is configured to couple the connection component to the ceiling flange in various height positions along a mounting axis, wherein the support comprises a cavity or at least a jaw which forms a coupling or guiding face to adjust to the height position. This results in the previously explained advantages.

The object described above is also achieved by a mounting apparatus for a stand device arrangeable in the operating room, wherein the mounting apparatus extends in a height direction along a mounting axis and is configured to hold a connection component of the stand device, wherein the mounting apparatus comprises at least one fastening portion including a plurality of fastening means, which are in particular formed identically, which are spaced in the height direction, wherein the at least one fastening portion is formed by a crosspiece arranged on an outside, outer contour or outer lateral surface of the mounting apparatus, in particular by a crosspiece protruding radially orthogonal to the height direction. This results in the previously explained advantages.

The object described above is also achieved by using a support according to the invention and/or a mounting apparatus according to the invention on a stand device arranged in the operating room, respectively, wherein the support and/or the mounting apparatus define different height positions along a mounting axis and position the stand device in a specific of the height positions. This results in previously explained advantages.

BRIEF DESCRIPTION OF THE SEVERAL VIEWS OF THE DRAWINGS

The invention will be explained in greater detail in the following figures with the help of exemplary embodiments. Illustrated are.

When describing the following figures, for reference numbers that are not explicitly explained in a figure, reference is made to the other figures.

DETAILED DESCRIPTION

Figure 1:
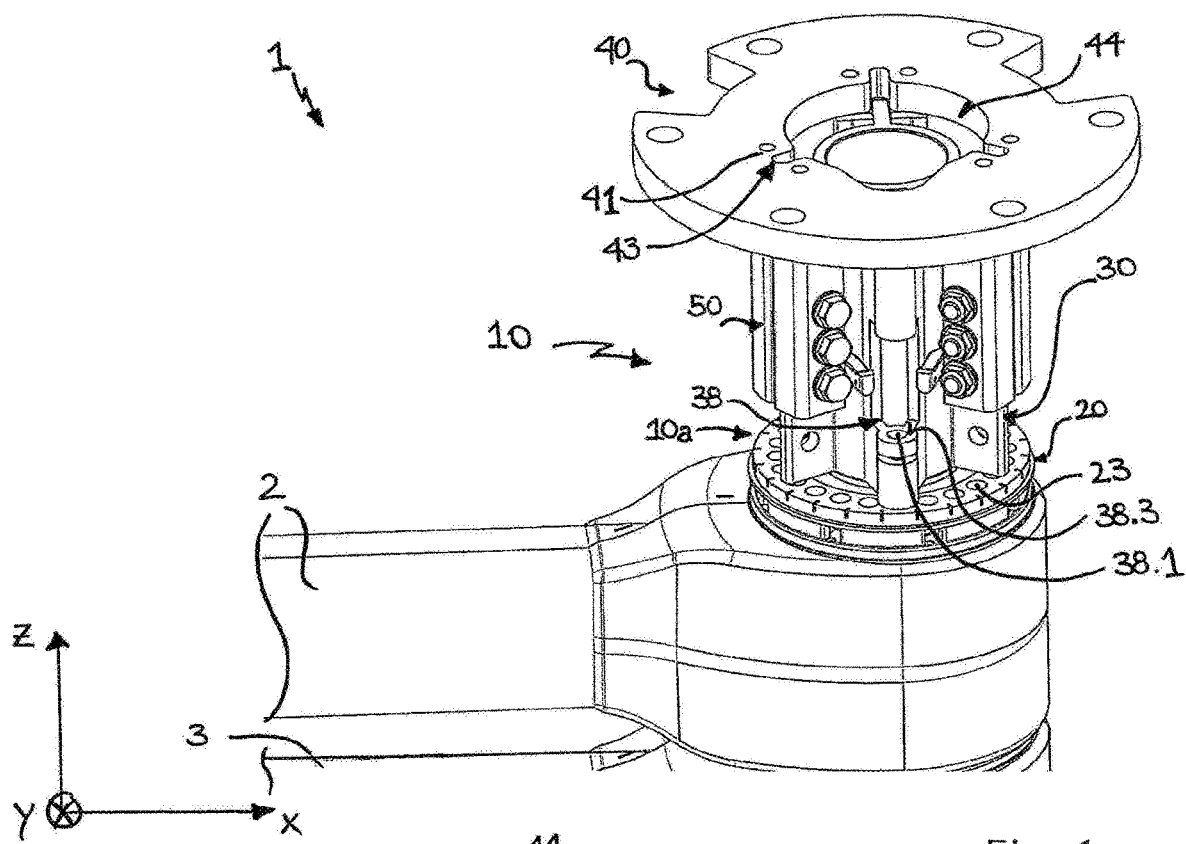
FIG. 1 a perspective side view a mounting device according to an exemplary embodiment of the invention in an arrangement mounted to a stand device.

In FIG. 1 a stand device for mounting on a ceiling is shown. The stand device 1 comprises a first carrier 2 and a second carrier 3 which are rotatably supported in a rotary bearing above one another about a mounting axis. In order to mount the stand device 1 on a (suspended)ceiling the two carriers 2, 3 are connected or coupled indirectly to a mounting device 10, which comprises an adaptable mechanism 10a formed as an adjustable rotational coupling. The stand device 1 may be mounted by using a ceiling flange 40, in particular of a flange plate type, on a ceiling or subceiling. The ceiling flange 40 comprises fastening means 41 adapted as openings, in particular (internally threaded) bores through which fasting means, for example screws, may be mounted. Mounting is performed by means of supports 50 ensuring a connection of the ceiling flange 40 to a mounting apparatus 30. The mounting apparatus 30 is in particular formed tube-like and comprises fastening portions 33 adapted as crosspieces protruding radially from the outer contour 31 thereof. At least 2, in the present embodiment exactly 3, fastening portions 33 are provided on the mounting apparatus 30, which cooperate with the corresponding number of supports 50 that are defined on the ceiling flange 40 and will be explained in detail in the following. The mounting apparatus 30 works together with an adjustment apparatus 20. The adjustment apparatus 20 may also be denoted as a flat ring. Hereto, the mounting apparatus 30 comprises a rotational lock, in particular a retainer 38 adapted as a tube-like portion, to accommodate a securing element. On an upper access region 38.3 a bolt or pin may be inserted through a through-bore 38.1 which works together with a specific coupling point 23 of the adjustment apparatus. Here, a plurality of coupling points 23 define a specific rotational position, respectively. The coupling points 23 may be configured as openings, bores, slots that are open on the sides, or recesses, for example.

Here a coordinate system indicates a horizontal direction and when mounted on the ceiling also a radial x direction and a vertical z direction.

The adjustment apparatus 20 may thus be supported on an inner ring of a ball bearing arranged in carrier 2 on carrier 2.

Figure 2:
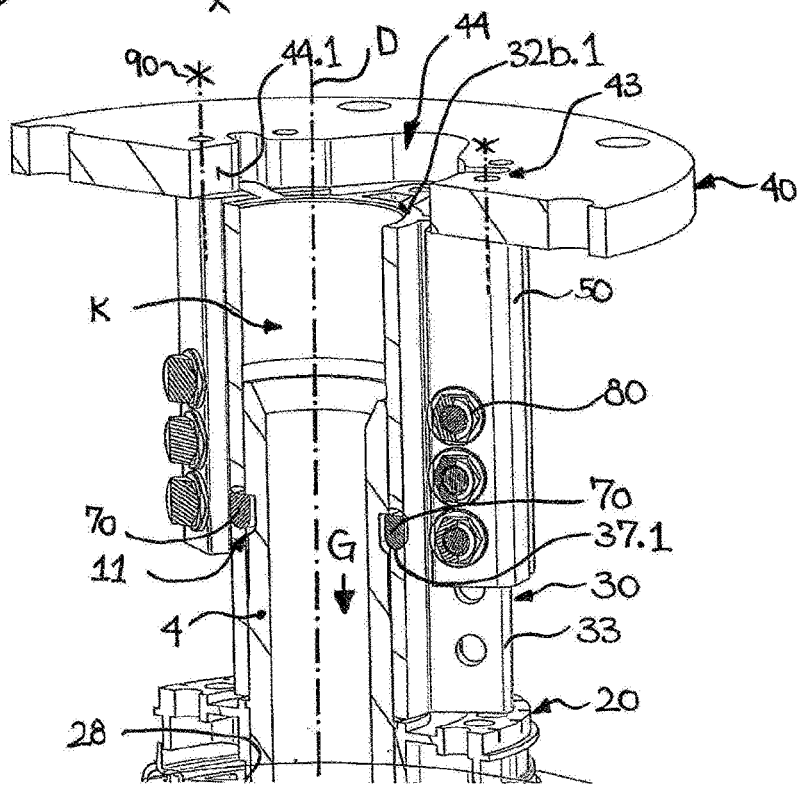
FIG. 2 a perspective side view the mounting device shown in FIG. 1.

FIG. 2 shows how the ceiling flange 40 may be connected to the mounting apparatus 30. The ceiling flange 40 comprises several radial grooves 43 that are formed to correspond geometrically to the fastening portions 33 of the mounting apparatus 30 adapted as crosspieces. In addition, the ceiling flange 40 comprises a passage 44 which is formed to correspond geometrically to the mounting apparatus 30, thus the mounting apparatus 30 is supported on the ceiling flange 40 or may be displaced in relation to the ceiling flange 40. The passage 44 is formed by an inner lateral surface 44.1 which comprises at least approximately the same peripheral line or cross-sectional geometry as the outer lateral surface 31 of the mounting apparatus. Preferably, the cross-sectional geometry of the inner lateral surface 44.1 is a little bit wider (larger diameter) as the cross-sectional geometry of the outer lateral surface 31. The inner lateral surface 44.1 may form a sliding bearing or a sliding surface for the mounting apparatus and enable the alignment or centering of the mounting apparatus 30 in relation to the ceiling flange 40. The inner lateral surface 44.1 may also facilitate mounting, in particular as the fastening means may easily be arranged in alignment to each other.

Here the ceiling flange 40 may be fastened to the supports 50 by using fastening elements 90, in particular screws, in a way that a weight G of the connection component 4, in particular a spindle, supported on the mounting apparatus 30 may be transferred via the mounting apparatus 30, the supports 50, and the fastening elements 90 to the ceiling flange 40 and thus to a ceiling or subceiling. The spindle 4 is supported in the cavity K formed by the mounting apparatus 30. Thus, a relative rotation of the spindle 4 in relation to the mounting apparatus 30 may be performed. The arrangement shown is rotatably supported about a mounting axis D in z direction. The relative rotatability can be prevented by means of the adjustment apparatus 20.

A relative axial movement or displacement downwards is prevented by providing an axial lock 11 on which the spindle 4 abuts. In the example shown, the axial lock 11 is formed by a plurality of securing elements 70, in particular latches, which are arranged tangentially to a mounting axis D and which engage with the spindle 4 and also with the mounting apparatus 30.

The mounting apparatus 30 may be mounted in different relative axial positions (height positions) relative to the supports 50 or to the ceiling flange 40, that is, by means of fastening elements 80, in particular screws, which engage with corresponding openings or through-bores on the respective fastening portion 33 or on the respective support 50.

Figure 3:
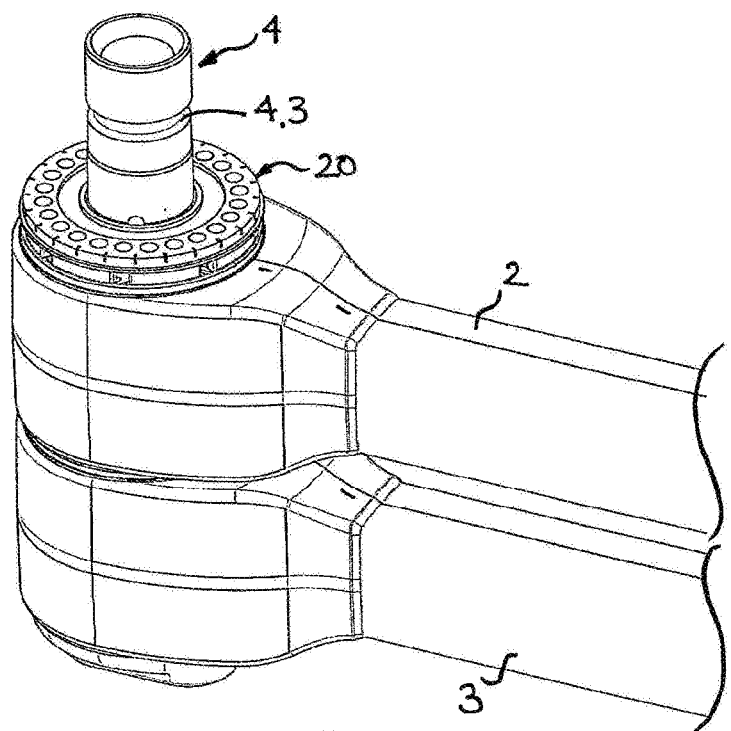
FIG. 3 a perspective side view from above an adjustment apparatus of the mounting device shown in FIG. 1, wherein the adjustment apparatus is arranged around a spindle of the stand device.

FIG. 3 shows how the spindle 4 is inserted in the cavity K of the mounting apparatus 30 from below. Here, the securing elements 70 described above may work together with a peripheral groove 4.3 in the end position. The spindle 4 is then rotatably supported on the groove 4.3, and in the cavity K in an axially fixed way.

Figure 4:
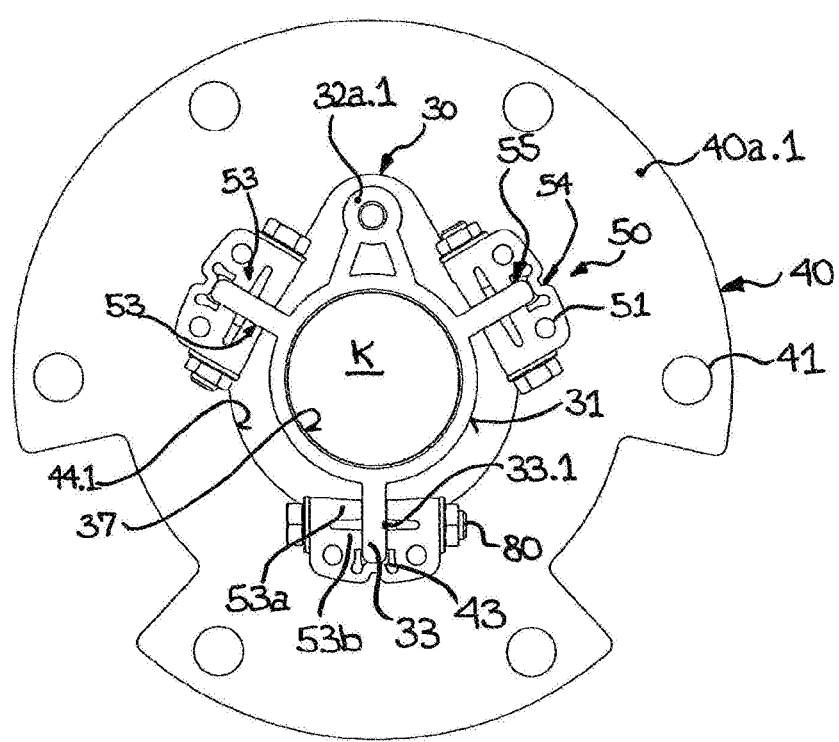
FIG. 4 plan view from below individual components of the mounting device shown in FIG. 1.
Figure 5:
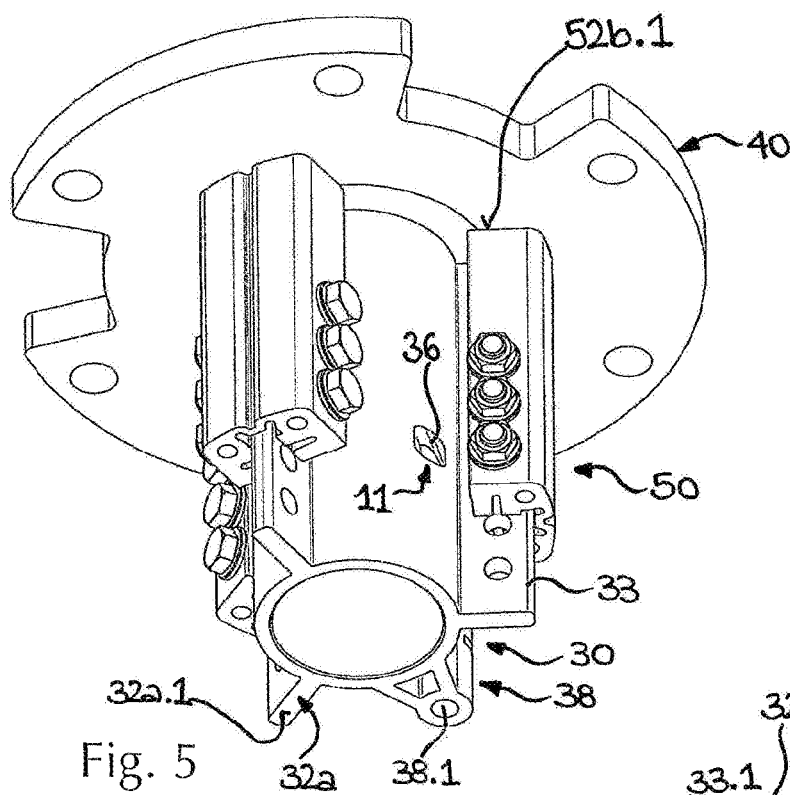
FIG. 5 a perspective side view individual components of the mounting device shown in FIG. 1.

In FIG. 4 a plane lower front face 42a.1 of the ceiling flange 40 is shown where the respective support 50 may abut on a planar upper front face 52b.1 (indicated in FIG. 5). The respective support 50 comprises continuous fastening means 51, in particular internally threaded bores, within which screws, for example, may engage. The respective fastening portion 33 abuts on opposite jaws 53. The jaws may be pressed against a respective radial flank 33.1 by means of the screws 80. Each jaw 53 includes single jaw portions 53a, 53*b*, which are adapted to ensure a secure or stressable connection of the respective support 50 with the mounting apparatus 30.

In addition, the respective support 50 includes a corrugation 54 that constitutes a face pointing outwards at least section-wise, and due to that the support 50 may be bent in a comparatively simple and flexible way and be easily mounted on the respective fastening portion 33.

The opposite jaws 53 define a fastening portion 55 adapted as radial cavity, in particular in a slot shape, that is formed to correspond geometrically to the respective fastening portion 33. The fastening portion 55 is surrounded by a centering surface 54.1 in the radial direction radially on the outside where a peripheral surface portion of the respective fastening portion 33 of the mounting apparatus 30 may abut. Here the fastening portions 33 extend in the radial direction outwards from a (sectionwise) cylindrical outer lateral surface 31 and extend said outer lateral surface. The mounting apparatus 30 comprises an at least section-wise cylindrical inner lateral surface 37 that defines the cavity K or surrounds it in the radial direction.

FIG. 5 shows the mounting apparatus 30 from a lower side in a state mounted on a ceiling flange 40. The retainer 38 for a rotational lock and also the individual fastening portions 33 define a lower front face 32*a*, which is formed by a planar lower front face 32*a*.1. On this front face 32*a*.1 the adjustment apparatus may abut. The mounting apparatus 30 may be adapted as a continuous cast profile, for example. On the lateral surface of the mounting apparatus 30 one or more passages 36 are provided, in particular in a tangential direction, which constitute a part of the axial lock 11.

Figure 6:
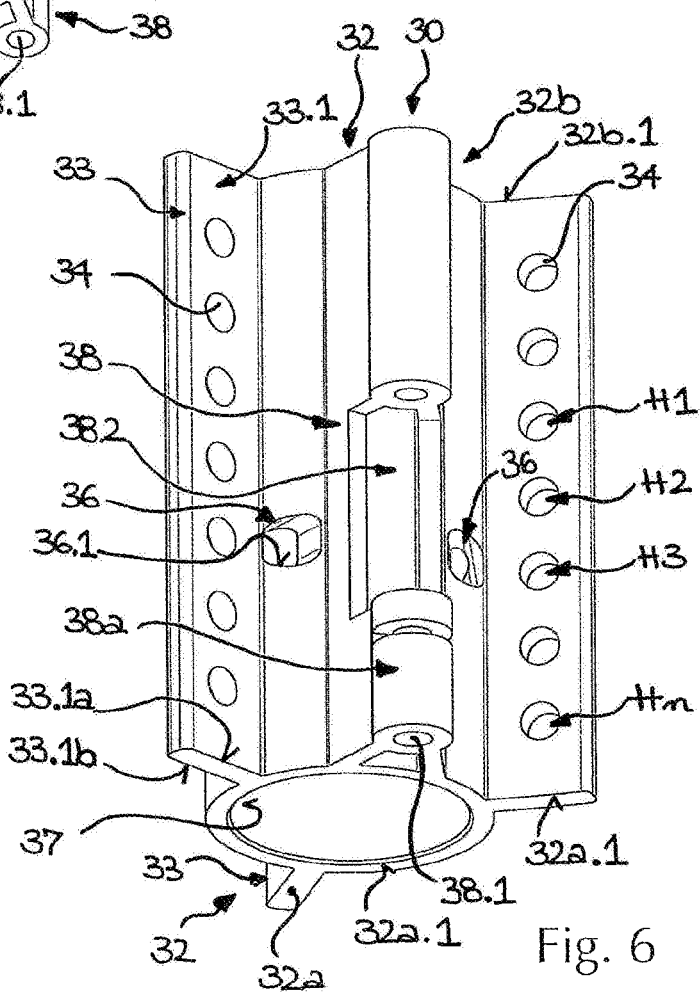
FIG. 6 a perspective side view a mounting apparatus of the mounting device shown in FIG. 1.

In FIG. 6 the mounting apparatus 30 is shown separately. The mounting apparatus 30 is formed as continuous cast profile and includes opposite front faces 32. Similar to the lower front face 32*a* an upper front face 32*b* is formed by a planar upper front face 32*b*.1. Along each of the fastening portions 33 a plurality of openings or fastening means 34 are provided, as for example threaded bores or bores. The passages 36 define a support surface 36.1, respectively, on which the securing element 70, shown in FIG. 2, may abut. The supporting surface 36.1 may also be formed at least partly by a chamfer, edge or milled recess 37.1 (see FIG. 2) formed on the inner lateral surface 37. A force flux path of a weight to be transferred passes through said support surfaces 36.1. The passages 36 adjoin radially inwards to at least two of the fastening portions 33. Each fastening portion 33 comprises opposite radial flanks 33.1*a*, 33.1*b*, in particular aligned parallel to each other. The rotational lock 38 or the retainer is formed as a locking tube portion. The rotational lock 38 includes a lower tube-like retainer portion 38*a*. The lower retainer portion 38*a* may be partitioned, in particular by a slot, wherein additional securing of a/the rotational lock element may be achieved by means of a spring connector. The retainer 38 includes an access 38.2 adapted as cutout. On said access or in the region of said access a bolt may be plugged into the through-bore 38.1 on the lower retainer portion 38*a*, that is, from above in the adjustment apparatus arranged on the lower front face 32*a*.1.

The fasting means 34 define different height positions H1, H2, H3, . . . , Hn, corresponding to the mounting points, where fastening elements may be mounted or supported, respectively. When fastened to the lowest mounting point Hn, which is arranged next to the lower side of the mounting apparatus 30, the mounting apparatus 30 or the stand device may be arranged in the highest height position.

Figure 7:
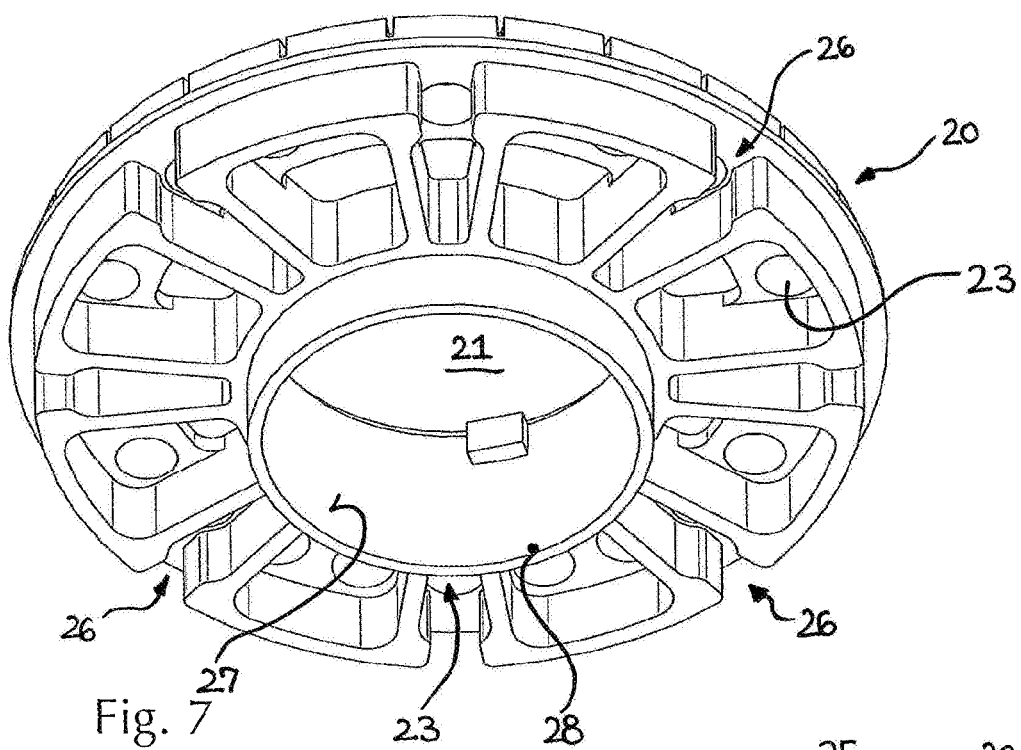
FIG. 7 a perspective view from below the adjustment apparatus shown in FIG. 1.
Figure 8:
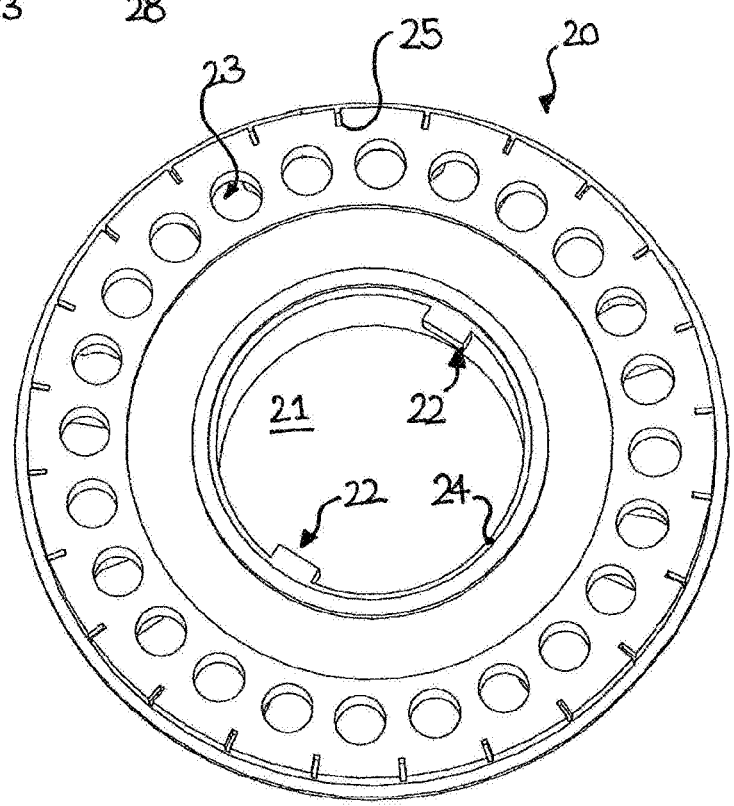
FIG. 8 a perspective view from above the adjustment apparatus shown in FIG. 7.

In FIG. 7 the adjustment apparatus 20 is shown from below. The adjustment apparatus 20 may also be denoted as flat ring. The spindle (not shown) may be passed through a passage 21. A rotational stop 22 (optionally also acting as centering) is arranged on an inner lateral surface 27, in particular adapted as a spring, that is formed to correspond geometrically to a respective groove of the spindle. Preferably two springs 22 are provided, as shown in FIG. 8. The springs 22 are arranged at an upper rim of the adjustment apparatus 20. On the lower side the adjustment apparatus 20 comprises a protruding rim 28 that facilitates an exact alignment or centering regarding the spindle due to a comparatively large axial extension. On the lower side of the adjustment apparatus 20 recesses 26 or radial slots are provided which a technician may access by using a tool (for example a screwdriver), in particular radially from outside, to rotate the adjustment apparatus 20 and thus the spindle. This way the relative rotational position may be adjusted, in particular without disassembly of any cover or enclosure. As already described regarding FIG. 1, the adjustment apparatus includes a plurality of coupling points 23 which are formed to correspond geometrically to a rotational lock means, in particular a bolt. According to a variant the coupling points 23 are formed as openings and have at least approximately the same diameter as the through-bore 38.1 shown in FIG. 6.

In FIG. 8 the adjustment apparatus 20 is shown from above. The adjustment apparatus 20 comprises an annular support surface 24 which may also be formed at least partly by the springs 22. The support surface 24 is formed to correspond geometrically to a radially protruding rim 4.4 (FIG. 9) of the spindle. In addition, on an outer periphery of the adjustment apparatus 20 fastening means for a cover or enclosure are provided. The fasting means are provided as slots 25 extending in the radial direction. Said configuration facilitates plugging in from above or from the side in the radial direction.

Figure 9:
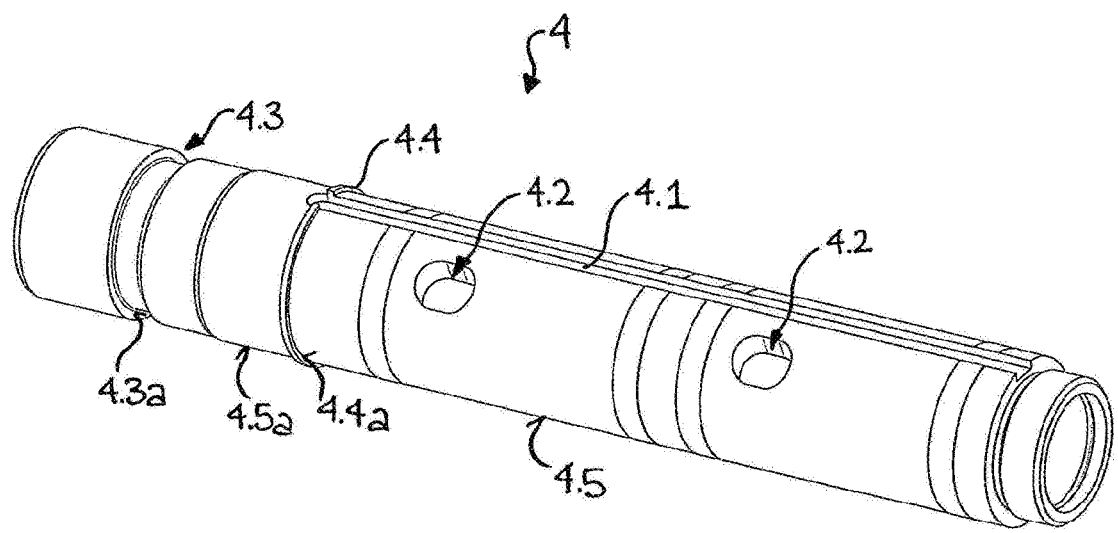
FIG. 9 a perspective view the spindle shown in FIG. 3.

In FIG. 9 the spindle 4 is shown in detail. The spindle 4 comprises two axial grooves 4.1 that are arranged in the longitudinal direction and opposite to one another. The respective axial groove extends to a step or radially protruding rim 4.4, thus springs may be pushed in the grooves 4.1 up to the rim 4.4. In addition, the spindle includes two recesses 4.2 that are arranged at an axial distance to one another and pass through an outer lateral surface 4.5. A cable, in particular a slip-ring cable, may be fed through the recesses 4.2, respectively. Above the rim 4.4 a centering surface portion 4.5*a* is provided by means of which the spindle 4 may be centered in the cavity K. The rim 4.4 defines an annular support surface 4.4*a* where the adjustment apparatus may abut. The peripheral groove 4.3 defines an annular support surface 4.3*a* by means of which the weight of a stand device may be transferred from the spindle 4 to an axial lock 11 (not shown).

Figure 10:
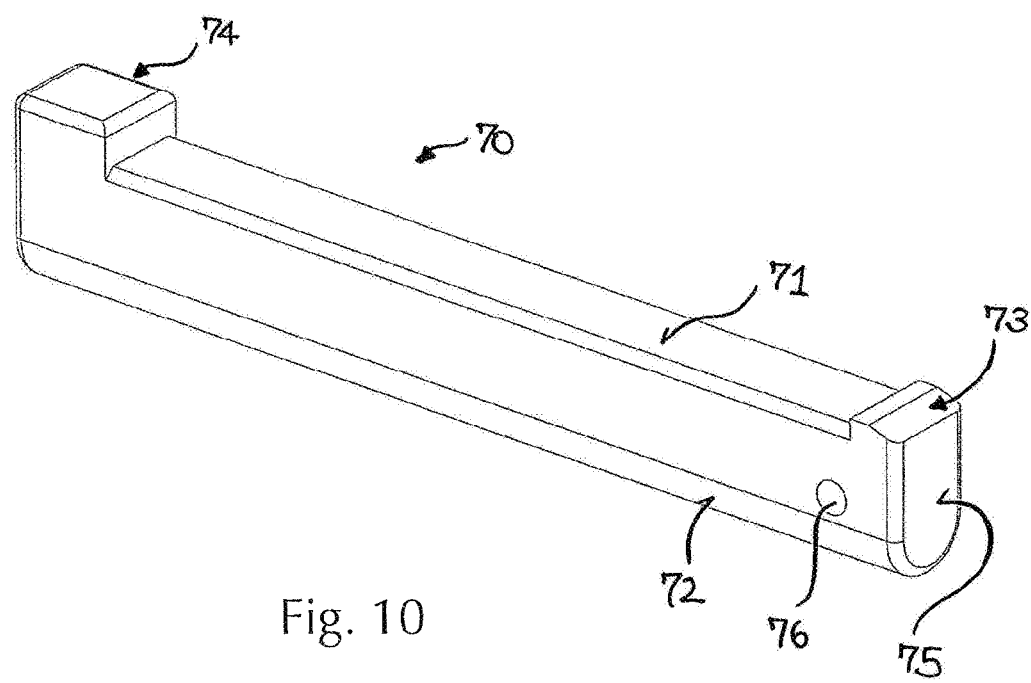
FIG. 10 a perspective view a securing element of the mounting device shown in FIG. 1.

In FIG. 10 the securing element 70 adapted as a latch is shown in detail. The latch 70 includes a top support surface 71 where the support surface 4.3*a* shown in FIG. 9 may abut. Further, the latch 70 includes a lower contact surface 72 that is curved in the present example, by means of which the latch 70 is supportable in the passage 36 on the mounting apparatus 30. The contact surface 72 is curved with a predefined curvature radius, whereby a minor notch effect may be ensured. The curved contact surface 72 may ensure a small surface pressure. The latch 70 has an U-shaped cross-section area 75 which basically has the same geometry along the complete length of the latch 70. A respective free end of the latch 70 includes a step 73, 74 that allows to secure the latch 70 in the passage 36. One of the steps is smaller than the other.

The step 73 is adapted as mounting chamfer and may prevent a slipping out of the latch 70. The step 74 also prevents a slipping out. The step 74 is preferably formed in a height at which the latch 70 may not be pushed through the corresponding passage, but is blocked on step 74.

In the region of one of the two free ends, the latch includes a through-bore 76 on which the latch 70 may be secured, in particular by means of a spring connector.

Figures 11A, 11B:
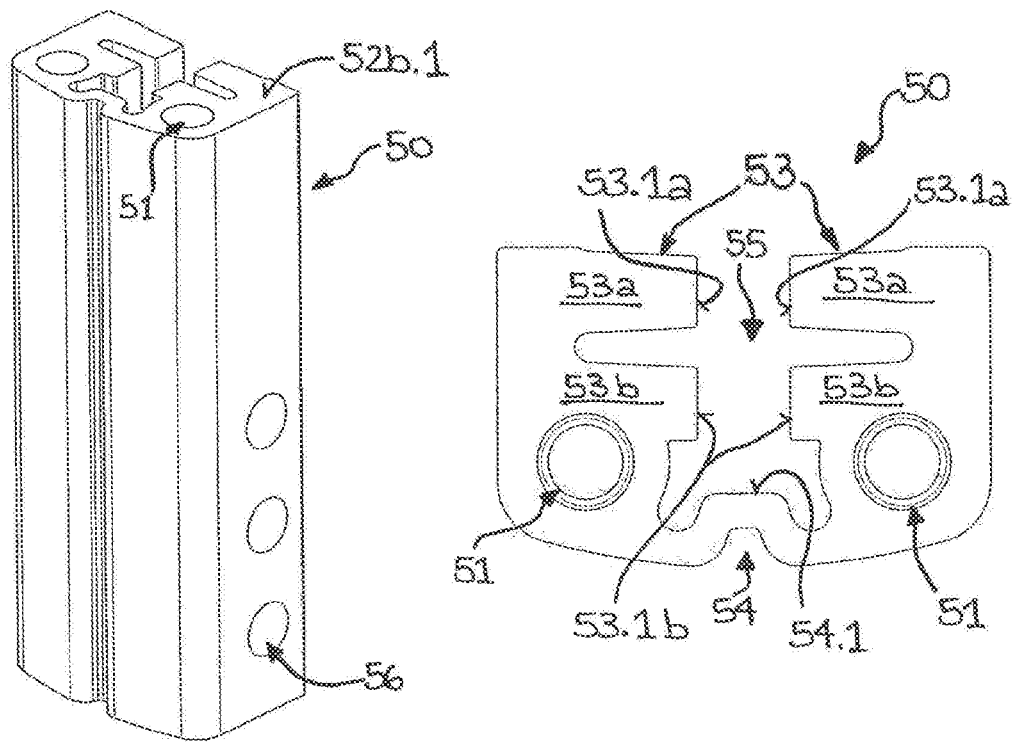
FIGS. 11A, 11B a perspective view and plan view a support of the mounting device shown in FIG. 1.

In FIGS. 11A and 11B a support 50 is shown which may be coupled with the mounting apparatus 30 shown in FIG. 6. In addition to the components already described above, the support 50 comprises fastening means which are formed as crosswise or tangentially aligned openings or through-bores. A respective fasting means, in particular the screws shown in FIG. 2, may be fed through both opposite jaws 43 and press the support 50 on a respective fastening portion 33 of the mounting apparatus 30, in particular by using nuts, thus a pressure is applied on the outer lateral surface of the jaws 53. Each jaw 53 comprises radial flanks 53.1a, 53.1b at the respective jaw portion. The radial flanks 53.1a, 53.1b are planar surface portions which are formed to correspond geometrically to the radial flanks 33.1 of the fastening portions 33.

Figure 12:
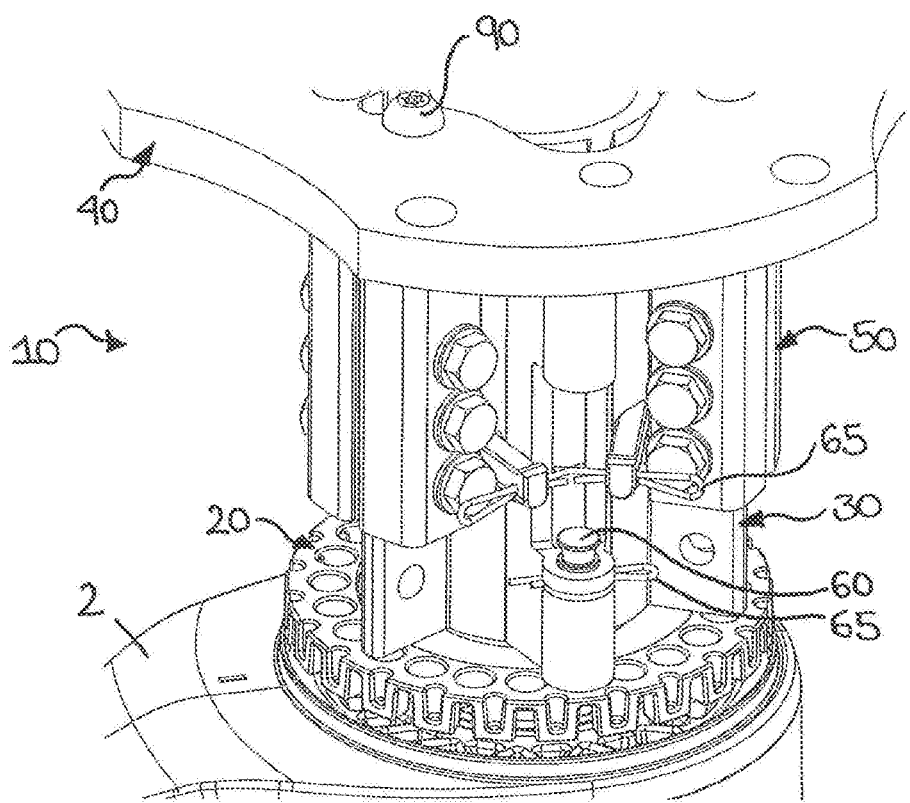
FIG. 12 a perspective view a mounting device according to a further exemplary embodiment of the invention in an arrangement mounted to a stand device including mounted securing elements.
Figure 13:
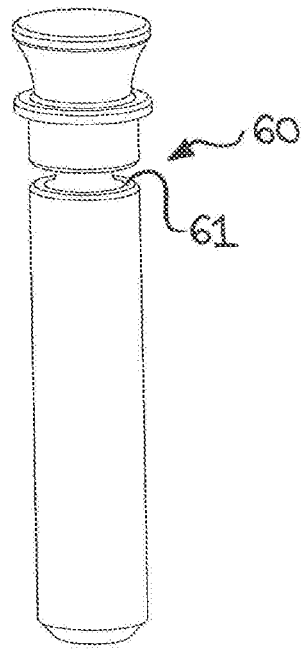
FIG. 13 a perspective view a rotational lock element configured to secure a rotational position of the mounting device.

FIG. 12 shows a mounting device 10 wherein a pin 60 (which may also be referred to as a rotational lock element) is secured on the mounting apparatus 30 by using a spring connector 65 in an engagement position with the adjustment apparatus 20. As can be seen in FIG. 13, the spring connector 65 engages with the groove 61 of the pin 60. The two latches 70 are also secured by corresponding spring connectors 65, wherein each spring connector engages with the corresponding through-bore of the respective latch 70.

Figure 14:
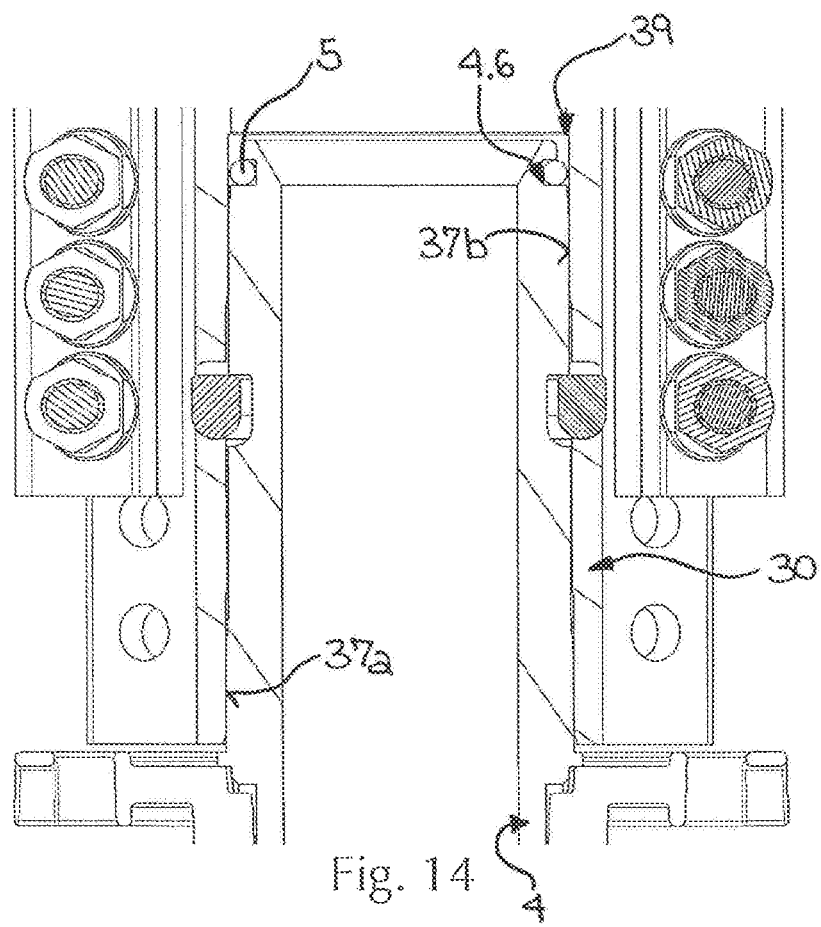
FIG. 14 a side section view a further exemplary embodiment of a mounting device.
Figure 15:
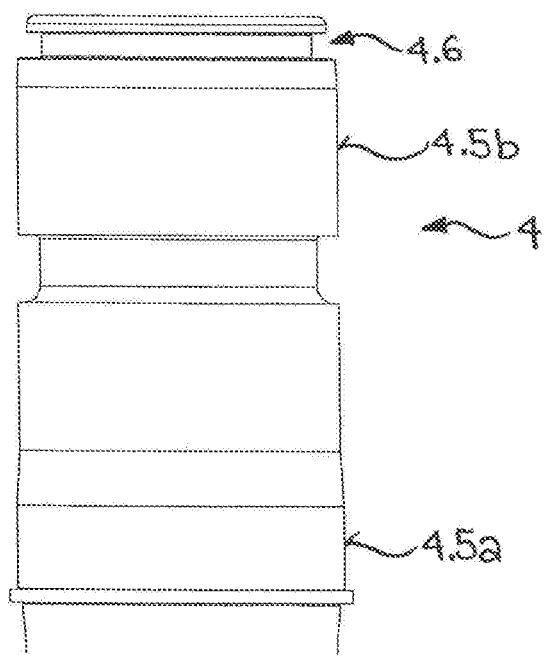
FIG. 15 a spindle specifically adapted for the mounting device shown in FIG. 14.

FIGS. 14 and 15 show how a simplified assembly may be performed by using two mating faces 37a, 37b and corresponding surface portions 4.5a, 4.5b on the spindle. The spindle 4 includes a step 4.6 where an O-ring 5 is arranged. Hereto, a corresponding step 39 is formed on the mounting apparatus 30. The second mating face 37b has an inner diameter that is smaller than that of the first mating face 37a. Thus, a spindle 4 may be mounted without the risk of jamming, and furthermore a support may be realized in a very robust way on surface portions 4.5a, 4.5b that are spaced far apart from one another.

LIST OF REFERENCE NUMBERS

1 Stand device—in particular a ceiling stand device
2 (First) carrier or carrier arm
3 (Second) carrier or carrier arm
4 Connection component, in particular spindle
4.1 Rotational lock, in particular a groove in the connection component, preferably an axial groove arranged in the longitudinal direction
4.2 Recess
4.3 Peripheral groove
4.3a Annular support surface
4.4 Step or radially protruding rim
4.4a Annular support surface
4.5 Outer lateral surface
4.5a Centering surface portion or first mating face
4.5b Second mating face
4.6 Groove for an O-ring on the free spindle end
5 O-ring
10 Mounting device
10a Adaptable mechanism, in particular, adjustable rotational coupling
11 Axial lock
20 Adjustment apparatus, in particular flat ring
21 Passage
22 Rotational lock, in particular spring
23 Coupling point for a respective rotational position, in particular opening or bore
24 Annular support surface
25 Fastening means for a cover, in particular an upper side slot
26 Recess, in particular on the lower side, that is accessible radially from outside
27 Inner lateral surface
28 Rim or centering
30 Mounting apparatus, in particular a basic body configured as a ceiling tube, preferably adapted as a continuous cast profile
31 Outer contour, in particular outer lateral surface
32 Front face
32a Lower front face
32a.1 Planar lower front face
32b Upper front face
32b.1 Planar upper front face
33 Fastening portion, in particular, crosspiece
33.1 Radial flank at the fastening portion
33.1a, 33.1b Opposite radial flanks, in particular arranged parallel to one another
34 Fastening means, in particular bore or threaded bore
36 Passage, in particular in a tangential or a radial direction
36.1 Support surface
37 Inner lateral surface
37a First mating face
37b Second mating face
37.1 Chamfer, edge or milled recess
38 Retainer for rotational lock element, in particular a locking tube
38a Lower retainer portion, in particular tube-like
38.1 Through-bore, in particular in an axial direction
38.2 Access, in particular cutout
38.3 Upper access region (interface)
39 Step
40 Ceiling flange, in particular flange plate
41 Fastening means or opening, preferably internally threaded bore
42a.1 Planar lower front face
43 Radial groove
44 Passage
44.1 Inner contour, in particular inner lateral surface
50 Support, in particular opening, preferably adapted as continuous cast profile
51 Fastening means, in particular axially aligned opening, preferably internally threaded bore
52b.1 Planar upper front face
53 Opposite jaws
53a, 523b Opposite jaw portions of a jaw
53.1a, 53.1b Guiding face or radial flank on the respective jaw portion
54 Corrugation
54.1 Centering surface
55 Fastening portion, in particular, radial cavity
56 Fastening means, in particular transversely or tangentially aligned opening, preferably through-bore
60 Pin
61 Groove
65 Spring connector
70 Securing element for axial lock, in particular a latch
71 Upper side support surface
72 Lower side contact surface 73 Step at a free end
74 Step at a free end
75 Cross-section area
76 Through-bore
80 Fastening element at support, in particular screw
90 Fastening element at flange plate, in particular screw
D Mounting axis
G Weight
H1, H2, H3 ... Hn Different height positions, defined by mounting points
K Cavity
x Radial direction or horizontal direction
y Transverse direction
z Longitudinal direction or axial direction or vertical direction The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A mounting device, comprising:
a spindle;
a mounting apparatus having a cavity extending therethrough, the spindle coupled to the mounting apparatus and at least partially received in the cavity, the mounting apparatus further including a retainer comprising a tube with a through-bore extending therethrough, the mounting apparatus further including a fastening portion extending along a complete length of the mounting apparatus in a longitudinal direction, the fastening portion including a plurality of openings extending along a complete length of the fastening portion;
a pin configured to be received in the through-bore of the tube of the retainer; and
a ceiling flange removably coupled to the mounting apparatus, wherein the ceiling flange is mountable to the mounting apparatus in different, predefined mounting positions relative to the mounting apparatus along a mounting axis.

2. The mounting device according to claim 1, wherein the fastening portion is a crosspiece extending from an outer contour of the mounting apparatus.

3. The mounting device according to claim 1, wherein the ceiling flange further comprises a passage, the passage having an inner diameter that is greater than or equal to an outer diameter of the mounting apparatus.

4. A mounting device, comprising:
a spindle;
a mounting apparatus having a body and a cavity extending therethrough, the spindle coupled to the mounting apparatus and at least partially received in the cavity, the mounting apparatus further including a retainer comprising a tube with a through-bore extending therethrough, the mounting apparatus further including a fastening portion extending from the body along a complete length of the body of the mounting apparatus and a plurality of openings in the fastening portion;
a pin configured to be received in the through-bore of the tube of the retainer;
a ceiling flange removably coupled to the mounting apparatus, wherein the ceiling flange is mountable to the mounting apparatus in different, predefined mounting positions relative to the mounting apparatus along a mounting axis; and
a support coupled to the ceiling flange, wherein the ceiling flange is a flange plate with a planar lower side front face abutting the support, the mounting apparatus mountable to the support in different, predefined mounting positions, wherein the ceiling flange extends beyond the support in a radial direction.

5. The mounting device according to claim 4, wherein the ceiling flange further comprises a plurality of threaded through-holes, which receive fasteners to fasten the mounting apparatus to the ceiling flange, and which are aligned in a longitudinal direction.

6. The mounting device according to claim 1, further comprising:
a support coupled to the ceiling flange, the mounting apparatus coupleable with the support in different positions relative to the ceiling flange, wherein the support comprises a fastening portion corresponding geometrically to the fastening portion of the mounting apparatus.

7. The mounting device according to claim 6, wherein the fastening portion of the support includes a radial cavity aligned in a radial direction with the fastening portion of the mounting apparatus at least partially received in the radial cavity of the fastening portion of the support.

8. The mounting device according to claim 1, wherein the fastening portion is a crosspiece radially protruding from an outside of the mounting apparatus, the mounting device further comprising:
a support coupled to the ceiling flange, wherein the support includes a fastening portion corresponding geometrically to the fastening portion of the mounting apparatus,
wherein the ceiling flange includes a lower face in abutting contact with the support, and
wherein the ceiling flange includes a plurality of openings that are aligned in the longitudinal direction to receive fasteners to mount the support on the ceiling flange.

9. The mounting device according to claim 1, wherein the mounting apparatus is a tube and the fastening portion of the mounting apparatus is a crosspiece including a plurality of flanks protruding radially from an outer contour of the tube of the mounting apparatus, the mounting device further comprising:
a plurality of supports coupled to the ceiling flange, wherein a number of the plurality of flanks correspond to a number of the plurality of supports coupled to the ceiling flange, each of the plurality of supports receiving a corresponding one of the plurality of flanks and one of a plurality of fasteners to couple the mounting apparatus to the plurality of supports.

10. The mounting device according to claim 9, further comprising:
an adjustment apparatus rotatably coupled to the mounting apparatus, the adjustment apparatus receiving a portion of the spindle to align the spindle in a predefined position relative to the mounting apparatus, wherein the adjustment apparatus is rotatably adjustable relative to the mounting apparatus around the mounting axis.

11. A system including the mounting device according to claim 1 or claim 4, the system further comprising:
a stand device arranged in an operation room and coupled to the mounting device, wherein the mounting device is adjustable between a plurality of different height positions along the mounting axis to arrange the stand device at different height positions corresponding to the plurality of different height positions of the mounting device.

12. A mounting device, comprising:
a spindle;
a mounting apparatus having a cavity extending vertically through a center of the mounting apparatus, the spindle coupled to the mounting apparatus and at least partially received in the cavity, the mounting apparatus further including a retainer comprising a tube with a through-bore extending vertically through a center of the retainer;
a pin configured to be received in the through-bore of the tube of the retainer; and
a ceiling flange removably coupled to the mounting apparatus, wherein the ceiling flange is mountable to the mounting apparatus in different, predefined mounting positions relative to the mounting apparatus along a mounting axis,
wherein the retainer includes a cutout through the retainer,
wherein a first vertical axis passes through a center of the through-bore of the retainer and a second vertical axis extends through a center of the cavity of the mounting apparatus, the first vertical axis spaced from the second vertical axis.

13. A mounting device, comprising:
a spindle;
a mounting apparatus having a cavity extending therethrough, the spindle coupled to the mounting apparatus and at least partially received in the cavity, the mounting apparatus further including a retainer comprising a tube with a through-bore extending therethrough;
a pin configured to be received in the through-bore of the tube of the retainer; and
a ceiling flange removably coupled to the mounting apparatus, wherein the ceiling flange is mountable to the mounting apparatus in different, predefined mounting positions relative to the mounting apparatus along a mounting axis,
wherein the retainer includes a cutout through the retainer,
wherein the retainer further includes a first portion and a second portion separated from the first portion in a vertical direction by the cutout with the first portion above the second portion in the vertical direction.

14. A mounting system, comprising:
a ceiling flange;
a plurality of supports coupled to the ceiling flange, each of the plurality supports including a radial cavity;
a mounting apparatus coupleable to the plurality of supports and having an outer surface and a cavity extending through the mounting apparatus, the mounting apparatus including:
a plurality of fastening portions, each fastening portion extending from the outer surface of the mounting apparatus, each of the fastening portions including a plurality of openings aligned in a longitudinal direction over a length of each of the plurality of fastening portions, wherein each of the plurality of fastening portions are at least partially received in a respective radial cavity of each of the plurality of supports; and
a retainer comprising a tube;
a spindle coupled to the mounting apparatus, a portion of the spindle received in the cavity of the mounting apparatus; and
an adjustment apparatus rotatably coupled to the mounting apparatus, the adjustment apparatus including a plurality of openings,
wherein the mounting apparatus is adjustable in the longitudinal direction relative to the plurality of supports and the ceiling flange between a plurality of different height positions corresponding to predefined locations of the plurality of openings of each of the plurality of fastening portions of the mounting apparatus relative to the plurality of supports where fasteners are mounted to couple the mounting apparatus to the plurality of supports in one of the plurality of different height positions.

15. The mounting system of claim 14 further comprising:
a pin, the pin inserted through the retainer and received in one of the plurality of openings of the adjustment apparatus.

16. A mounting system, comprising:
a ceiling flange;
a plurality of supports coupled to the ceiling flange, each of the plurality of supports including a cavity and a plurality of openings;
a mounting apparatus coupleable to the plurality of supports and including a cavity extending through the mounting apparatus, the mounting apparatus including a plurality of fastening portions extending from the mounting apparatus, each fastening portion including a plurality of openings aligned in a longitudinal direction over a length of each of the plurality of fastening portions, wherein each of the fastening portions of the plurality of fastening portions are at least partially received in the cavity of a respective one of the plurality of supports, the mounting apparatus further including a retainer comprising a tube configured to receive a pin, the retainer positioned between successive ones of the plurality of fastening portions,
wherein the mounting apparatus is adjustable relative to the plurality of supports and the ceiling flange between a plurality of positions corresponding to predefined locations where the plurality of openings of each fastening portion align with the plurality of openings of each of the supports for receiving a plurality of fasteners through the plurality of openings of each fastening portion and the plurality of openings of each of the supports to couple the mounting apparatus to the plurality of supports.

17. The mounting system of claim 16 further comprising:
a spindle coupled to the mounting apparatus and at least partially received in the cavity of the mounting apparatus.

18. The mounting device of claim 4 wherein the ceiling flange extends in a radial direction and the support extends from the ceiling flange perpendicular to the ceiling flange, the fastening portion of the mounting apparatus structured to be received by the support.

19. The mounting device of claim 12 wherein the pin includes a groove extending into the pin structured to align with the cutout through the retainer when the pin is received is in the retainer.

20. The mounting device of claim 13 wherein the mounting apparatus includes a plurality of fastening portions, the retainer coupled to a first one and a second one of the plurality of fastening portions and spaced from the cavity of the mounting apparatus in a radial direction.

21. The mounting device of claim 20 wherein the retainer is spaced equidistant from the first one and the second one of the plurality of fastening portions.

22. The mounting device of claim 13 wherein the pin further includes a groove extending into the pin configured to align with the cutout between the first portion and the second portion of the retainer.

* * * * *